(12) United States Patent
Yamada et al.

(10) Patent No.: US 11,611,227 B2
(45) Date of Patent: Mar. 21, 2023

(54) POWER SUPPLY UNIT FOR AEROSOL INHALER, AND CONTROL METHOD AND CONTROL PROGRAM OF THE SAME

(71) Applicant: JAPAN TOBACCO INC., Tokyo (JP)

(72) Inventors: Manabu Yamada, Tokyo (JP); Takeshi Akao, Tokyo (JP); Hajime Fujita, Tokyo (JP)

(73) Assignee: JAPAN TOBACCO INC., Tokyo (JP)

(*) Notice: Subject to any disclaimer, the term of this patent is extended or adjusted under 35 U.S.C. 154(b) by 0 days.

(21) Appl. No.: 16/668,890

(22) Filed: Oct. 30, 2019

(65) Prior Publication Data
US 2020/0128883 A1 Apr. 30, 2020

(30) Foreign Application Priority Data
Oct. 31, 2018 (JP) .............................. JP2018-204705

(51) Int. Cl.
*H02J 7/00* (2006.01)
*A61M 15/00* (2006.01)

(52) U.S. Cl.
CPC ......... *H02J 7/0063* (2013.01); *A61M 15/009* (2013.01); *A61M 2205/50* (2013.01); *A61M 2205/702* (2013.01); *A61M 2205/8206* (2013.01)

(58) Field of Classification Search
CPC ................ H02J 7/0063; A61M 15/009; A61M 2205/50; A61M 2205/72
USPC ....................................................... 131/328
See application file for complete search history.

(56) References Cited

U.S. PATENT DOCUMENTS

| 9,450,439 B2 * | 9/2016 | Hongo | H01M 10/052 |
| 9,601,800 B2 * | 3/2017 | Nakamoto | H01M 10/441 |
| 9,991,551 B2 * | 6/2018 | Nakamoto | H02J 7/00712 |
| 10,168,389 B2 * | 1/2019 | Fujiki | H01M 4/366 |
| 10,806,180 B2 * | 10/2020 | Otiaba | H01M 4/5825 |
| 2004/0241534 A1 * | 12/2004 | Suzuki | H02J 7/0071 429/50 |
| 2005/0274715 A1 * | 12/2005 | Johnson | A61F 7/007 219/548 |
| 2008/0054908 A1 | 3/2008 | Suzuki | |
| 2011/0084702 A1 * | 4/2011 | Mori | H01M 10/441 324/430 |
| 2017/0027234 A1 * | 2/2017 | Farine | A24F 40/60 |
| 2018/0271155 A1 * | 9/2018 | Baker | A24F 40/60 |

(Continued)

FOREIGN PATENT DOCUMENTS

| CN | 102043132 A | 5/2011 |
| CN | 108135268 A | 6/2018 |

(Continued)

OTHER PUBLICATIONS

Office Action dated Jun. 8, 2020 by the European Patent Office in counterpart European patent Application No. 19206196.8.

(Continued)

*Primary Examiner* — Alexander Gilman
(74) *Attorney, Agent, or Firm* — Sughrue Mion, PLLC

(57) ABSTRACT

A power supply unit for an aerosol inhaler includes: a power supply that is able to discharge power to a load for generating an aerosol from an aerosol source; and a control unit that is configured to control the power supply. The control unit acquires a deteriorated state or a failure state of the power supply based on an internal resistance of the power supply.

11 Claims, 13 Drawing Sheets

(56) References Cited

U.S. PATENT DOCUMENTS

| | | | | |
|---|---|---|---|---|
| 2018/0375177 A1* | 12/2018 | Mori | ............... | H02J 7/0068 |
| 2019/0380395 A1* | 12/2019 | Takeuchi | ............... | H02J 7/0036 |
| 2020/0107581 A1* | 4/2020 | Akao | ............... | H02M 3/158 |
| 2020/0107582 A1* | 4/2020 | Mizuguchi | ............... | A24F 40/53 |
| 2020/0108213 A1* | 4/2020 | Akao | ............... | A24F 40/53 |
| 2020/0128883 A1* | 4/2020 | Yamada | ............... | H01M 10/48 |
| 2020/0212516 A1* | 7/2020 | Akao | ............... | H01M 10/488 |
| 2020/0212517 A1* | 7/2020 | Akao | ............... | G01R 31/382 |
| 2020/0237006 A1* | 7/2020 | Akao | ............... | H02J 7/005 |
| 2020/0281277 A1* | 9/2020 | Akao | ............... | A24F 40/90 |

FOREIGN PATENT DOCUMENTS

| | | |
|---|---|---|
| EP | 3 583 859 A1 | 12/2019 |
| JP | 2005-19385 A | 1/2005 |
| JP | 4389910 B2 | 12/2009 |
| JP | 2013-242324 A | 12/2013 |
| JP | 2017-514463 A | 6/2017 |
| JP | 2018-55793 A | 4/2018 |
| JP | WO2018/163261 A1 | 9/2018 |
| JP | 2018-160960 A | 10/2018 |
| WO | 2017/150195 A1 | 9/2017 |
| WO | 2018/163261 A1 | 9/2018 |

OTHER PUBLICATIONS

Communication dated Oct. 8, 2019 issued by the Japanese Patent Office in Application No. 2018-204705.
Communication dated Oct. 26, 2021 issued by the Korean Patent Office in counterpart Korean Application No. 10-2021-0003068.
Office Action dated Feb. 12, 2019 by the Japanese Patent Office in counterpart Japanese Patent Application No. 2018-204705.
Office Action dated Jul. 9, 2019 by the Japanese Patent Office in counterpart Japanese Patent Application No. 2018-204705.
Communication dated Feb. 19, 2020 issued by the Japanese Patent Office in Application No. 2018-204705.
Office Action dated Dec. 30, 2020 by the State Intellectual Property Office of P.R. China in counterpart Chinese Patent Application No. 201911056168.3.

* cited by examiner

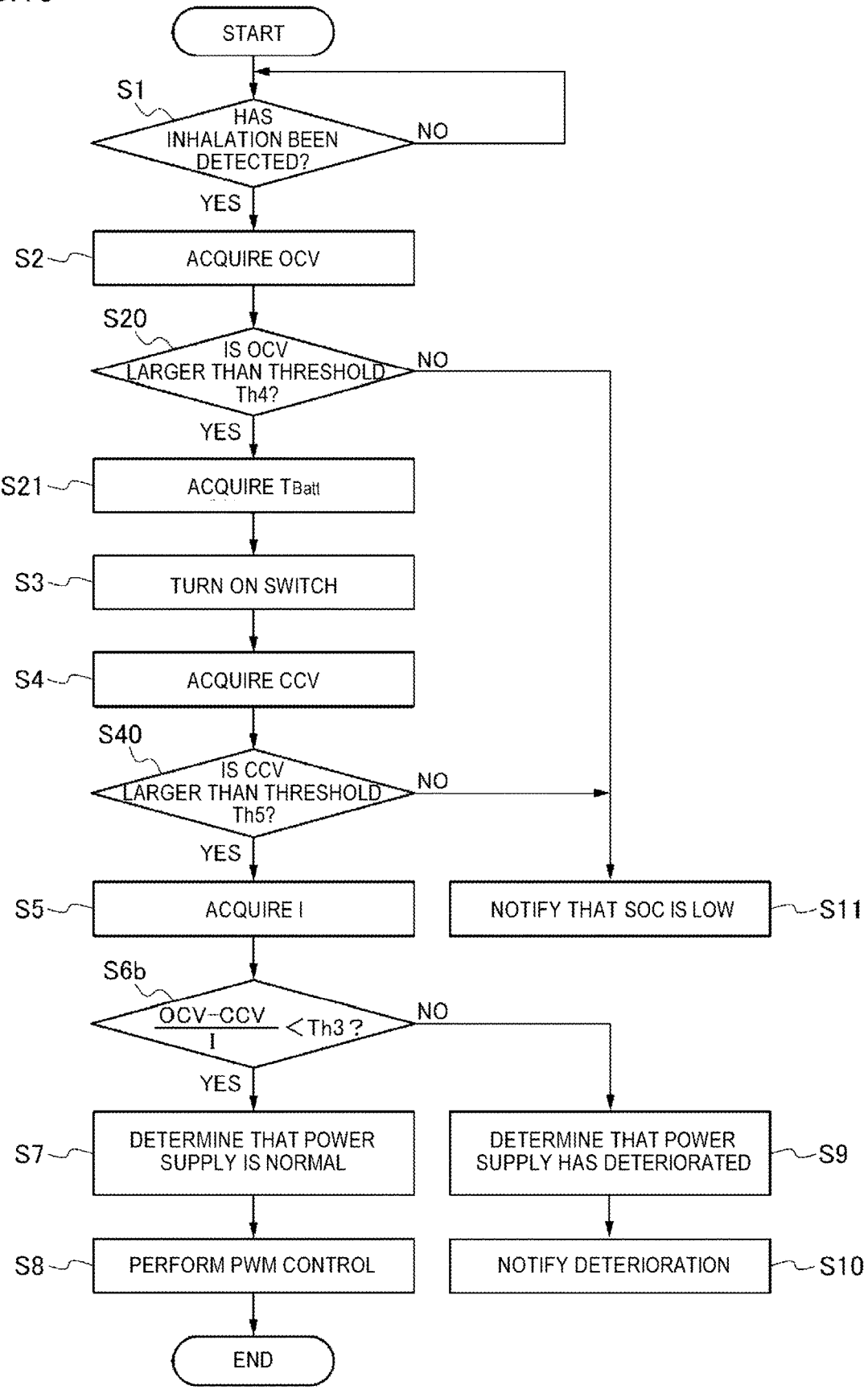

POWER SUPPLY UNIT FOR AEROSOL INHALER, AND CONTROL METHOD AND CONTROL PROGRAM OF THE SAME

CROSS-REFERENCE TO RELATED APPLICATIONS

This application is based upon and claims the benefit of priority from prior Japanese patent application No. 2018-204705, filed on Oct. 31, 2018, the entire contents of which are incorporated herein by reference.

TECHNICAL FIELD

The present invention relates to a power supply unit for an aerosol inhaler, and a control method and control program of the power supply unit.

BACKGROUND ART

An aerosol generating device disclosed in Patent Literature 1 measures a voltage between terminals of an electric energy supply source in the course of use of the aerosol generating device, and monitors whether the voltage is lower than a threshold at an arbitrary time point by comparing the voltage with the threshold voltage. However, by only measuring the voltage drop, it is not possible to determine whether it is just required to recharge the battery, or the battery has deteriorated so much that replacement is required. For this reason, the aerosol generating device disclosed in Patent Literature 1 tracks the voltage drop from a status of a usage record, and issues a signal to a user when the battery replacement is required.

Patent Literature 1: JP-A-2017-514463

The aerosol generating device disclosed in Patent Literature 1 requires a lot of time to determine deterioration of the battery. For this reason, a control method of performing determination on deterioration or failure of a battery in a shorter time is required.

An object of the present invention is to provide a power supply unit for an aerosol inhaler, and a control method and control program of the power supply unit, capable of appropriately grasping a deteriorated state or failure state of a power supply in a shorter time.

SUMMARY OF INVENTION

According to an aspect of the invention, there is provided a power supply unit for an aerosol inhaler, the power supply unit comprising: a power supply that is able to discharge power to a load for generating an aerosol from an aerosol source; and a control unit that is configured to control the power supply, wherein the control unit acquires a deteriorated state or a failure state of the power supply based on an internal resistance of the power supply.

BRIEF DESCRIPTION OF DRAWINGS

FIG. 8 is a view illustrating a circuit equivalent to the electrical circuit of the aerosol inhaler of FIG. 6 when the switch is on.

FIG. 15 is a control flow chart of deterioration diagnosis control of a third modification.

DESCRIPTION OF EMBODIMENTS

Figure 1:
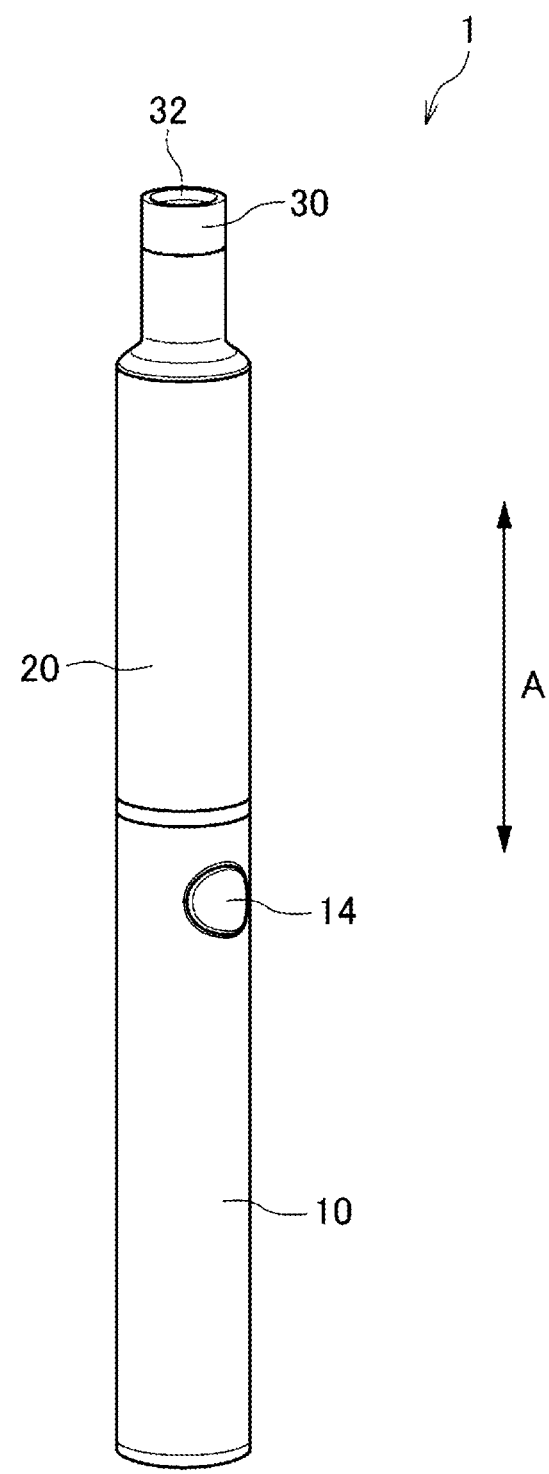
FIG. 1 is a perspective view for an aerosol inhaler equipped with a power supply unit of an embodiment of the present invention.
Figure 2:
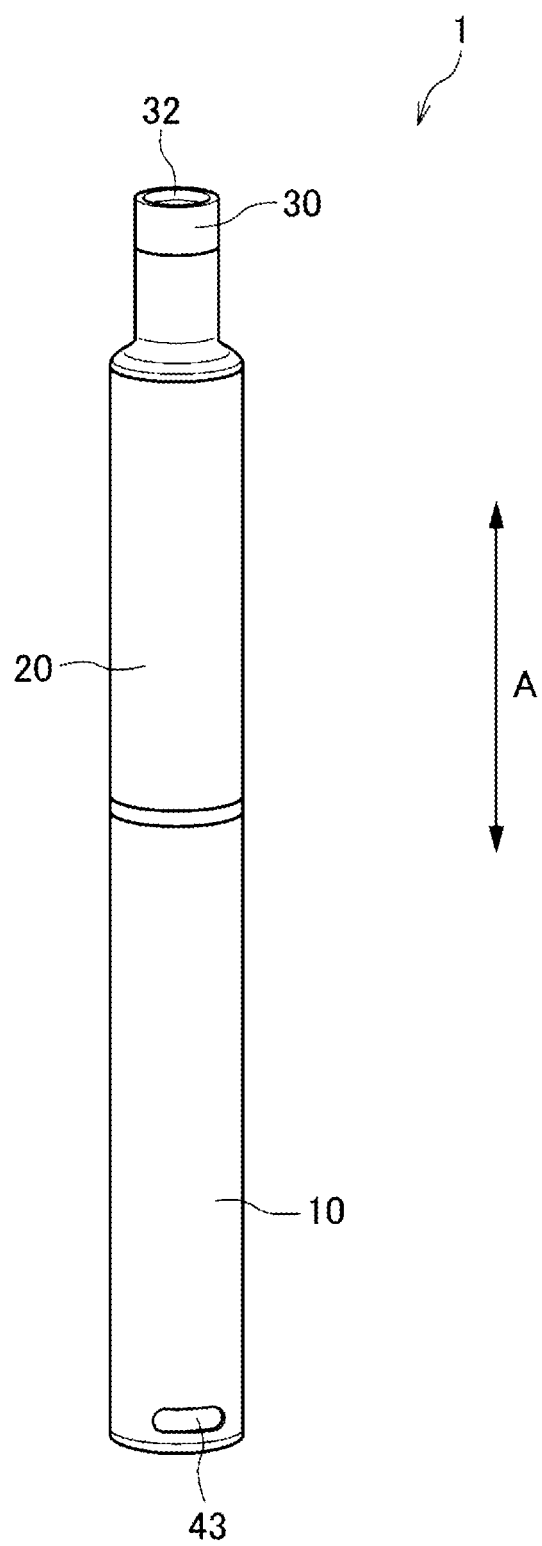
FIG. 2 is another perspective view of the aerosol inhaler of FIG. 1.

Hereinafter, a power supply unit for an aerosol inhaler according to an embodiment of the present invention will be described. First of all, the aerosol inhaler equipped with the power supply unit will be described with reference to FIG. 1 to FIG. 3.

(Aerosol Inhaler)

An aerosol inhaler 1 is a device for inhaling a flavor without combustion, and has a rod shape extending along a certain direction (hereinafter, referred to as the longitudinal direction A). The aerosol inhaler 1 includes a power supply unit 10, a first cartridge 20, and a second cartridge 30 which are arranged in the order along the longitudinal direction A. The first cartridge 20 can be attached to and detached from the power supply unit 10, and the second cartridge 30 can be attached to and detached from the first cartridge 20. In other words, the first cartridge 20 and the second cartridge 30 can be individually replaced.

(Power Supply Unit)

Figure 3:
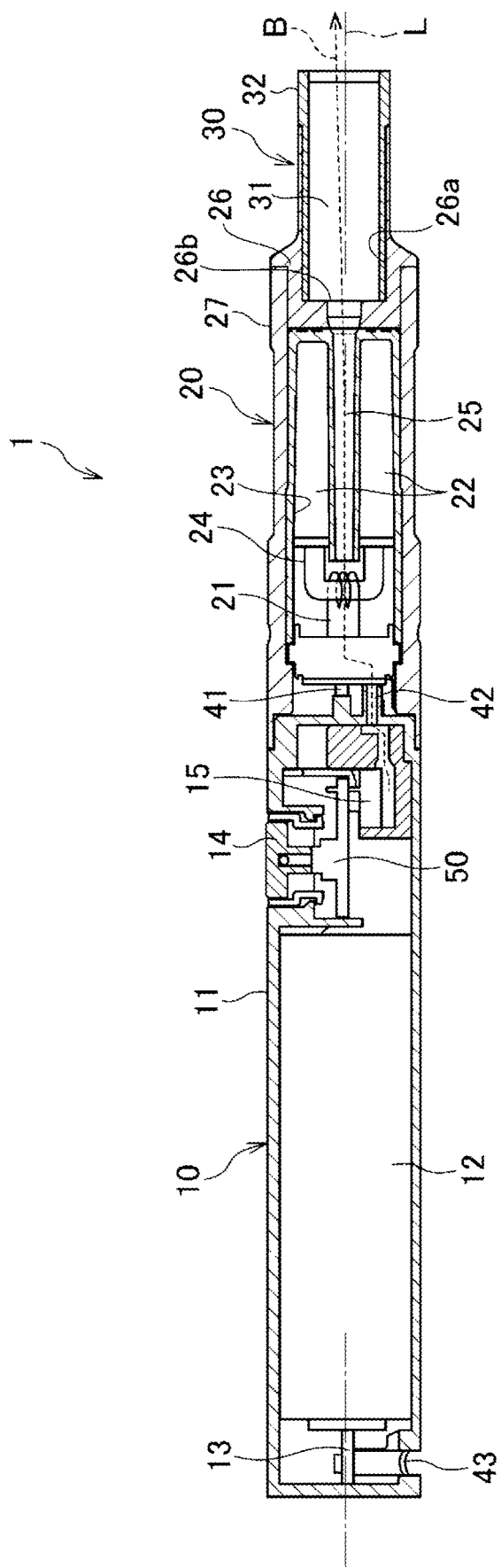
FIG. 3 is a cross-sectional view of the aerosol inhaler of FIG. 1
Figure 4:
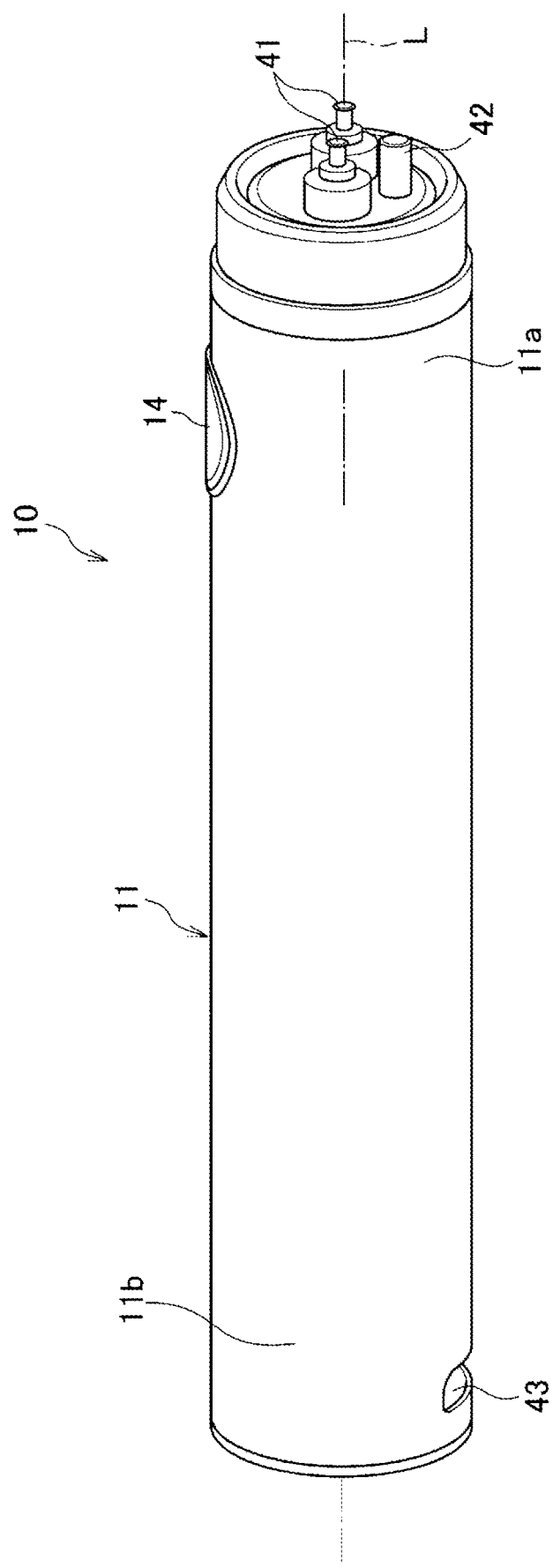
FIG. 4 is a perspective view of the power supply unit.

The power supply unit 10 of the present embodiment includes a power supply 12, a charger 13, a control unit 50, various sensors, and so on in a cylindrical power supply unit case 11, as shown in FIG. 3 and FIG. 4. The power supply 12 is a chargeable secondary battery, an electric double-layer capacitor, or the like, and is preferably a lithium-ion battery.

On a top part 11a of the power supply unit case 11 positioned on one end side in the longitudinal direction A (the first cartridge (20) side), a discharging terminal 41 is provided. The discharging terminal 41 is provided so as to protrude from the top surface of the top part 11a toward the first cartridge 20, and is configured to be able to be electrically connected to a load 21 of the first cartridge 20.

Further, on a part of the top surface of the top part 11a in the vicinity of the discharging terminal 41, an air supply part 42 for supplying air to the load 21 of the first cartridge 20 is provided.

On a bottom part 11b of the power supply unit 10 positioned on the other end side in the longitudinal direction (the opposite side to the first cartridge 20), a charging terminal 43 able to be electrically connected to an external power supply 60 (see FIG. 6) capable of charging the power supply 12 is provided. The charging terminal 43 is provided on the side surface of the bottom part 11b such that at least one of USB terminals, micro USB terminals, and Lightning terminals can be connected thereto.

However, the charging terminal 43 may be a power receiving part able to receive power from the external power supply 60 in a non-contact manner. In this case, the charging terminal 43 (the power receiving part) may be composed of a power receiving coil. The wireless power transfer system may be an electromagnetic induction type, or may be a magnetic resonance type. Also, the charging terminal 43 may be a power receiving part able to receive power from the external power supply 60 without any contact point. As another example, the charging terminal 43 may be configured such that at least one of USB terminals, micro USB terminals, and Lightning terminals can be connected thereto and the above-mentioned power receiving part is included therein Also, on the side surface of the top part 11a of the power supply unit case 11, an operation unit 14 which the user can operate is provided so as to face the opposite side to the charging terminal 43. More specifically, the operation unit 14 and the charging terminal 43 are symmetric with respect to the point of intersection of a straight line connecting the operation unit 14 and the charging terminal 43 and the center line L of the power supply unit 10 in the longitudinal direction A. The operation unit 14 is composed of a button type switch, a touch panel, or the like, and is used to perform various processes such as a process of activating and shutting off the control unit 50 and various sensors according to user's intention to use. In the vicinity of the operation unit 14, the control unit 50 and an inhalation sensor 15 for detecting a puff action are provided.

The charger 13 is disposed close to the charging terminal 43, and controls charging power from the charging terminal 43 to be input to the power supply 12. The charger 13 includes a converter for converting direct current, which is applied from an inverter 61 or the like (see FIG. 6) provided for converting alternating current into direct current on a charging cable which is connected to the charging terminal 43, into direct current having a different magnitude, a voltmeter, an ammeter, a processor, and so on.

Figure 5:
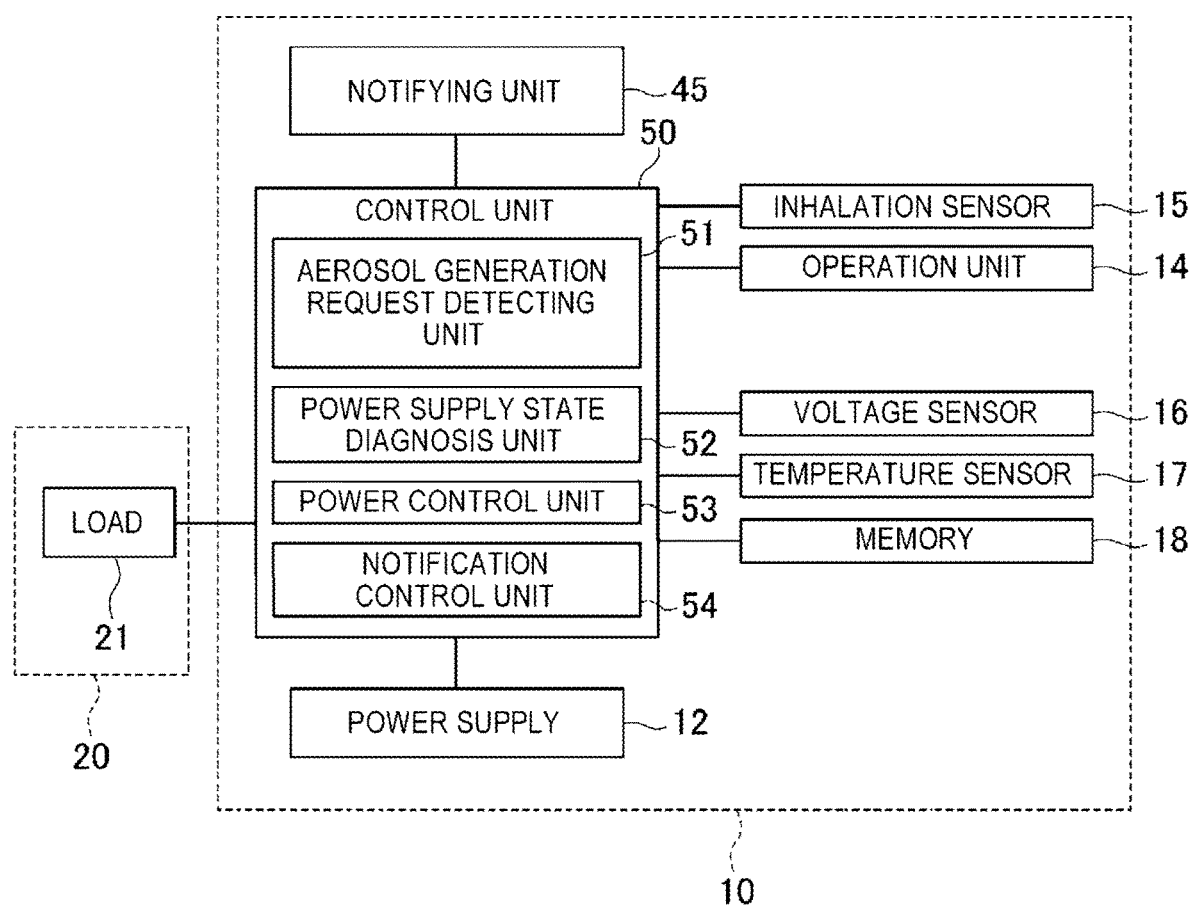
FIG. 5 is a block diagram of the power supply unit.

The control unit 50 is connected to various sensor devices, such as the inhalation sensor 15 for detecting a puff (inhaling) action, a voltage sensor 16 for measuring the voltage of the power supply 12, and a temperature sensor 17, the operation unit 14, and a memory 18 for storing the number of puff actions, the time for which power has been applied to the load 21, and so on, as shown in FIG. 5, and performs a variety of control on the aerosol inhaler 1. The inhalation sensor 15 may be configured with a capacitor microphone, a pressure sensor, or the like. The control unit 50 is specifically a processor (a computer). More specifically, the structure of this processor is an electric circuit configured by combining circuit elements such as semiconductor elements. The details of the control unit 50 will be described below.

Also, in the power supply unit case 11, an air intake (not shown in the drawings) for taking in air is formed. The air intake may be formed around the operation unit 14, or may be formed around the charging terminal 43.

(First Cartridge)

As shown in FIG. 3, the first cartridge 20 includes a reservoir 23 for storing an aerosol source 22, the electric load 21 for atomizing the aerosol source 22, a wick 24 for drawing the aerosol source from the reservoir 23 toward the load 21, an aerosol channel 25 for an aerosol generated by atomizing the aerosol source 22 to flow toward the second cartridge 30, an end cap 26 for storing a part of the second cartridge 30.

The reservoir 23 is formed so as to surround the aerosol channel 25, and holds the aerosol source 22. In the reservoir 23, a porous member such as a resin web or cotton may be stored, and the porous member may be impregnated with the aerosol source 22. The aerosol source 22 includes a liquid such as glycerin, propylene glycol, or water.

The wick 24 is a liquid holding member for drawing the aerosol source 22 toward the load 21 using capillarity, and is configured with, for example, glass fiber, a porous ceramic, or the like.

The load 21 atomizes the aerosol source 22 without combustion by power which is supplied from the power supply 12 through the discharging terminal 41. The load 21 is configured with a heating wire wound with a predetermined pitch (a coil). However, the load 21 needs only to be an element capable of atomizing the aerosol source 22, thereby generating an aerosol, and is, for example, a heating element or an ultrasonic wave generator.

Examples of the heating element include a heating resistor, a ceramic heater, an induction heating type heater, and so on.

The aerosol channel 25 is provided on the downstream side of the load 21 on the center line L of the power supply unit 10.

The end cap 26 includes a cartridge storage part 26a for storing a part of the second cartridge 30, and a connecting passage 26b for connecting the aerosol channel 25 and the cartridge storage part 26a.

(Second Cartridge)

The second cartridge 30 holds a flavor source 31. The end part of the second cartridge 30 on the first cartridge (20) side is stored in the cartridge storage part 26a provided in the end cap 26 of the first cartridge 20, so as to be able to be removed. The end part of the second cartridge 30 on the opposite side to the first cartridge (20) side is configured as an inhalation port 32 for the user. However, the inhalation port 32 does not necessarily need to be configured integrally with the second cartridge 30 so as not to be separable from the second cartridge, and may be configured to be able to be attached to and detached from the second cartridge 30. If the inhalation port 32 is configured separately from the power supply unit 10 and the first cartridge 20 as described above, it is possible to keep the inhalation port 32 sanitary.

The second cartridge 30 adds a flavor to the aerosol generated by atomizing the aerosol source 22 by the load 21, by passing the aerosol through the flavor source 31. As a raw material piece which constitutes the flavor source, a compact made by forming shredded tobacco or a tobacco raw material into a grain shape can be used. The flavor source 31 may be configured with a plant (such as mint or a herbal medicine, or a herb) other than tobacco. To the flavor source 31, a flavoring agent such as menthol may be added.

The aerosol inhaler 1 of the present embodiment can generate an aerosol containing the flavor by the aerosol source 22, the flavor source 31, and the load 21. In other words, the aerosol source 22 and the flavor source 31 can be referred to as an aerosol generation source for generating an aerosol.

The configuration of the aerosol generation source which can be used in the aerosol inhaler 1 is not limited to the configuration in which the aerosol source 22 and the flavor source 31 are configured separately, and may be a configuration in which the aerosol source 22 and the flavor source 31 are formed integrally, a configuration in which the flavor source 31 is omitted and the aerosol source 22 contains a substance which can be contained in the flavor source 31, a configuration in which the aerosol source 22 contains a medical substance or the like instead of the flavor source 31, or the like.

In the aerosol inhaler 1 configured as described above, as shown by an arrow B in FIG. 3, air entering from the intake (not shown in the drawings) formed in the power supply unit case 11 passes through the air supply part 42, and passes near the load 21 of the first cartridge 20. The load 21 atomizes the aerosol source 22 drawn from the reservoir 23 by the wick 24. The aerosol generated by atomizing flows through the aerosol channel 25 together with the air entering from the intake, and is supplied to the second cartridge 30 through the connecting passage 26b. The aerosol supplied to the second cartridge 30 passes through the flavor source 31, whereby the flavor is added, and is supplied to the inhalation port 32.

Also, in the aerosol inhaler 1, a notifying unit 45 for notifying a variety of information is provided (see FIG. 5). The notifying unit 45 may be configured with a light emitting element, or may be configured with a vibrating element, or may be configured with a sound output element. Alternatively the notifying unit 45 may be a combination of two or more elements of light emitting elements, vibrating elements, and sound output elements. The notifying unit 45 may be provided in any one of the power supply unit 10, the first cartridge 20, and the second cartridge 30; however, it is preferable that the notifying unit be provided in the power supply unit 10. For example, the area around the operation unit 14 is configured to have translucency to permit light which is emitted by a light emitting element such as an LED to pass through.

(Electronic Circuit)

Now, the electric circuit of the power supply unit 10 will be described with reference to FIG. 6.

The power supply unit 10 includes the power supply 12, a positive electrode side discharging terminal 41a and a negative electrode side discharging terminal 41b which constitute the discharging terminal 41, a positive electrode side charging terminal 43a and a negative electrode side charging terminal 43b which constitute the charging terminal 43, the control unit 50 which is connected between the positive electrode side of the power supply 12 and the positive electrode side discharging terminal 41a and between the negative electrode side of the power supply 12 and the negative electrode side discharging terminal 41b, the voltage sensor 16 which measures the voltage of the power supply 12, the charger 13 which is disposed on the power transmission path between the charging terminal 43 and the power supply 12, and a switch 19 which is disposed on the power transmission path between the power supply 12 and the discharging terminal 41. The switch 19 is configured with, for example, a MOSFET, and is opened and closed by control of the control unit 50 on the gate voltage. The control unit 50 can determine that the external power supply 60 is connected to the charging terminal 43, for example, on the basis of a variation in small current flowing in the control unit 50.

Figure 6:
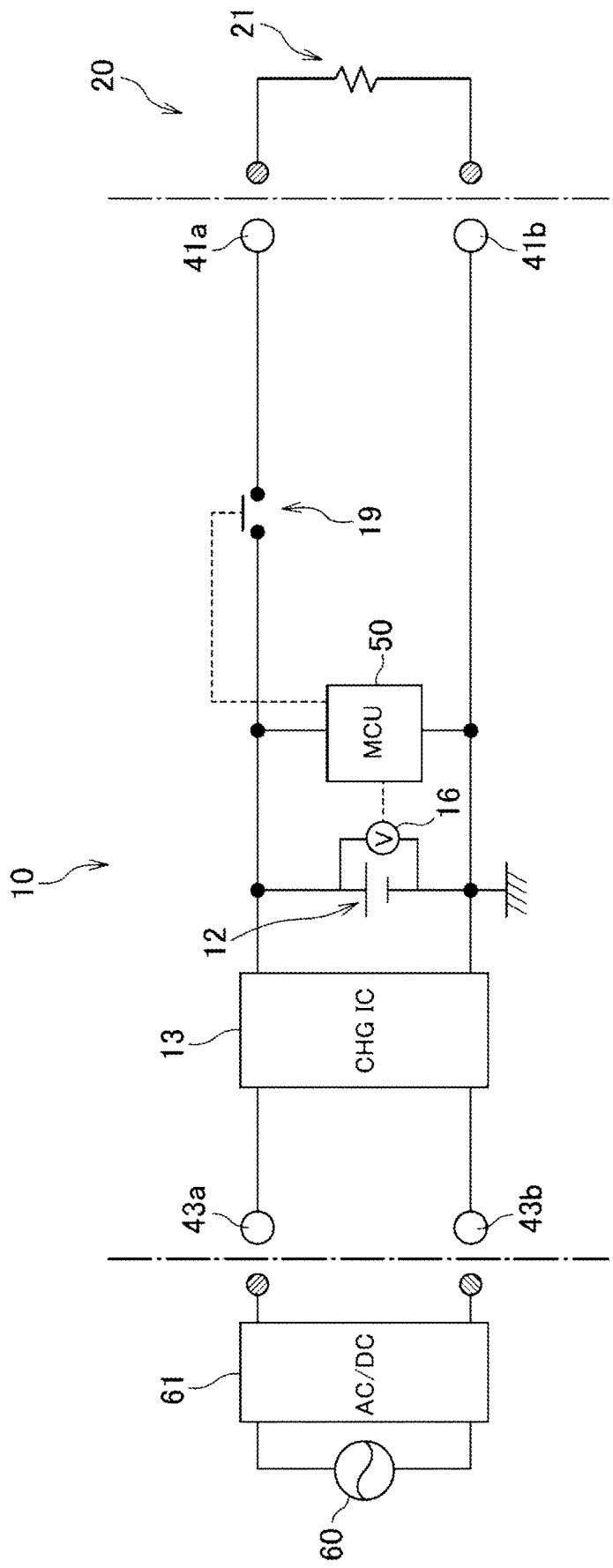
FIG. 6 is an electric circuit diagram of the aerosol inhaler.

In the electric circuit diagram of the power supply unit 10 shown in FIG. 6, the control unit 50 and the voltage sensor 16 are separate parts. Alternatively, the control unit 50 may have the function of measuring the voltage of the power supply 12. Also, in the electric circuit of the power supply unit 10 shown in FIG. 6, the switch 19 is provided between the positive electrode side of the power supply 12 and the positive electrode side discharging terminal 41a. Instead of this so-called plus control type, the switch 19 may be a minus control type which is provided between the negative electrode side discharging terminal 41b and the negative electrode side of the power supply 12.

(Control Unit)

Now, the configuration of the control unit 50 will be described in more detail.

As shown in FIG. 5, the control unit 50 includes an aerosol generation request detecting unit 51, a power supply state diagnosis unit 52, a power control unit 53, and a notification control unit 54.

The aerosol generation request detecting unit 51 detects a request for aerosol generation on the basis of the output result of the inhalation sensor 15. The inhalation sensor 15 is configured to output the value of a variation in the pressure in the power supply unit 10 caused by inhalation of the user through the inhalation port 32. The inhalation sensor 15 is, for example, a pressure sensor for outputting an output value (for example, a voltage value or a current value) according to atmospheric pressure which varies according to the flow of air which is sucked from the intake (not shown in the drawings) toward the inhalation port 32 (i.e. a puff action of the user).

The power supply state diagnosis unit 52 acquires the deteriorated state (State of Health) or failure state of the power supply 12. The power supply state diagnosis unit 52 can acquire the amount of power stored in the power supply 12 (State of Charge), in addition to the deteriorated state or failure state of the power supply 12. Deterioration diagnosis control and failure diagnosis control of the power supply state diagnosis unit 52 will be described below.

The notification control unit 54 controls the notifying unit 45 such that the notifying unit notifies a variety of information. For example, the notification control unit 54 may control the notifying unit 45 such that the notifying unit notifies the timing to replace the power supply 12, on the basis of diagnosis of the power supply state diagnosis unit 52 on deterioration of the power supply 12, or may control the notifying unit 45 such that the notifying unit notifies the timing to charge the power supply 12, on the basis of diagnosis of the power supply state diagnosis unit 52 on the amount of power stored in the power supply 12. Alternatively, the notification control unit 54 may control the notifying unit 45 in response to detection of a timing to replace the second cartridge 30, such that the notifying unit notifies the timing to replace the second cartridge 30. The notification control unit 54 notifies a timing to replace the second cartridge 30, on the basis of the number of puff actions and the cumulative time for which power has been supplied to the load 21, stored in the memory 18.

The power control unit 53 controls discharging of the power supply 12 through the discharging terminal 41 by switching on and off the switch 19 if the aerosol generation request detecting unit 51 detects the request for aerosol generation.

The power control unit 53 performs control such that the amount of aerosol which is generated by atomizing the aerosol source by the load 21 falls in a desired range, i.e. such that the amount of power which is supplied from the power supply 12 to the load 21 falls in a predetermined range. Specifically, the power control unit 53 controls switching on and off of the switch 19 by, for example, PWM (Pulse Width Modulation) control. Alternatively, the power control unit 53 may control switching on and off of the switch 19 by PFM (Pulse Frequency Modulation) control.

The power control unit 53 may stop supply of power from the power supply 12 to the load 21 if a predetermined period passes after start of supply of power to the load 21. In other words, even while the user is actually performing a puff action, if the puff period exceeds a certain period, the power control unit 53 stops supply of power from the power supply 12 to the load 21. The certain period is determined to suppress variation in user's puff period. The power control unit 53 controls the on/off duty ratio of the switch 19 for one puff action, according to the amount of power stored in the power supply 12. For example, the power control unit 53 controls the interval between ON times for which power is supplied from the power supply 12 to the load 21 (see the pulse interval T1 in FIG. 12) and controls the length of each ON time for which power is supplied from the power supply 12 to the load 21 (see the pulse width T2 in FIG. 12).

Also, the power control unit 53 detects an electric connection between the charging terminal 43 and the external power supply 60, and controls charging of the power supply 12 through the charging terminal 43.

Here, in the power supply 12 which is used in the aerosol inhaler 1, if charging and discharging are repeated, the internal resistance increases, whereby the power supply 12 deteriorates. If the power supply 12 deteriorates, the full charge capacity of the power supply 12 may decrease, and it may not be possible to store sufficient power to inhale an aerosol. For this reason, it is required to appropriately grasp the deteriorated state of the power supply 12.

(Deterioration Diagnosis Control)

Therefore, the power supply state diagnosis unit 52 acquires the deteriorated state of the power supply 12 by deterioration diagnosis control to be described below. In general, the deteriorated state of a power supply 12 is expressed as the ratio of the full charge capacity of the power supply when it is in a deteriorated state to the full charge capacity of the power supply when it is brand new. However, it is difficult to accurately acquire the full charge capacity of the power supply 12. For this reason, in the deterioration diagnosis control which is performed by the power supply state diagnosis unit 52, the deteriorated state of the power supply 12 is acquired on the basis of the internal resistance of the power supply 12. However, some types of deterioration diagnosis control to be described below and the like may be configured as programs which can execute them, and be read into the power supply unit 10, and be executed by the power supply unit 10.

First of all, the internal resistance R of the power supply 12 will be described taking, as an example, the case where the power supply 12 is a lithium-ion battery, with reference to FIG. 7 to FIG. 10.

Figure 7:
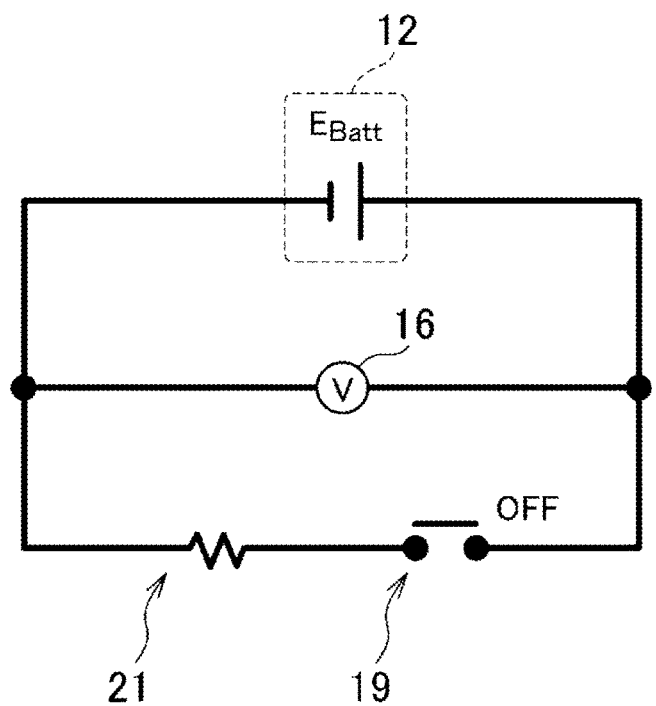
FIG. 7 is a simple electric circuit diagram of the aerosol inhaler of FIG. 6 when a switch is off.

FIG. 7 is a view simply illustrating the electric circuit of the aerosol inhaler 1 of FIG. 6 when the switch 19 is off. The measurement value of the voltage sensor 16 when the switch 19 is off, i.e. the open circuit voltage OCV is equal to the electromotive force $E_{Batt}$ of the power supply 12.

Figure 8:
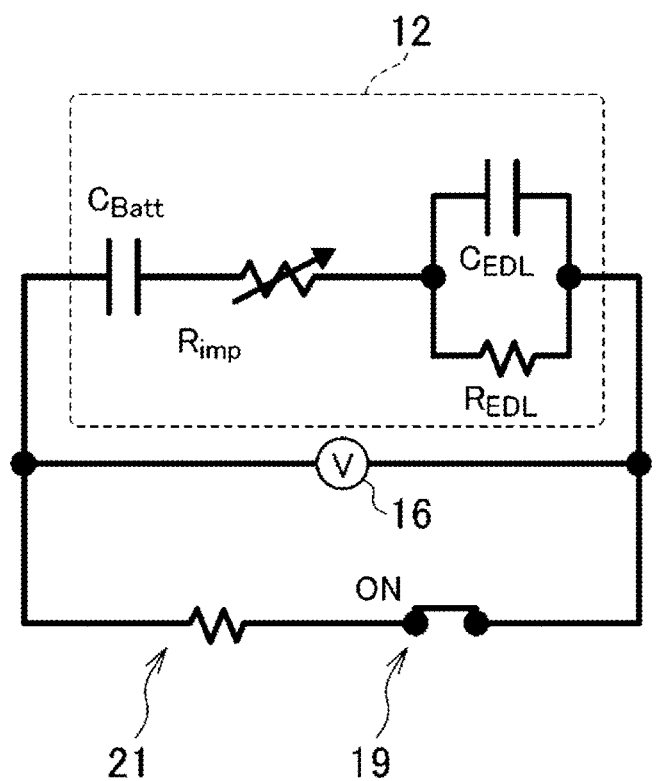

FIG. 8 is a view illustrating a circuit equivalent to the electrical circuit of the aerosol inhaler 1 of FIG. 6 when the switch 19 is on (when the electric circuit constitutes an open circuit). A reference symbol "$C_{Batt}$" represents a capacitor having the same electromotive force as that of the power supply 12, and a reference symbol "$R_{imp}$" represents the inter-electrode internal resistance between the electrodes which is applied to lithium ions when the lithium ions move between the electrodes, and a reference symbol "$C_{EDL}$" represents a capacitor showing electric double-layer capacitance at the electrode interfaces, and a reference symbol "$R_{EDL}$" represents reaction resistance when lithium ions move in the interfaces between the electrodes and the electrolytic solution. The reaction resistance $R_{EDL}$ and the electric double-layer capacitor $C_{EDL}$ are provided in parallel on the downstream side of the capacitor $C_{Batt}$ the inter-electrode internal resistance $R_{imp}$, whereby the inter-electrode internal resistance $R_{imp}$ constitutes a direct current (DC) component, and the reaction resistance $R_{EDL}$ constitutes a primary delay (AC) component.

The measurement value of the voltage sensor 16 when the switch 19 is on, i.e. the closed circuit voltage CCV is the value obtained by subtracting a loss caused by the inter-electrode internal resistance $R_{imp}$ and a loss caused by the reaction resistance $R_{EDL}$ from the electromotive force of the power supply 12.

Figure 9:
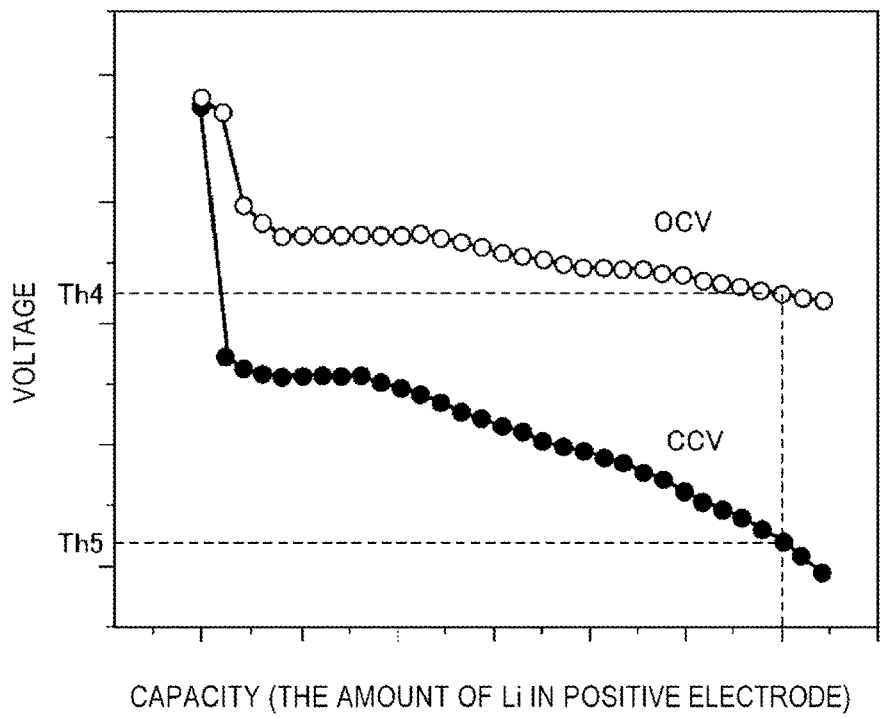
FIG. 9 is a graph illustrating the relation of open circuit voltage, closed circuit voltage, and the remaining amount of a power supply.

Therefore, as shown in FIG. 9, with respect to the same remaining amount of the power supply 12, the relation in which the open circuit voltage OCV is larger than the closed circuit voltage CCV is established. FIG. 9 shows the relation between the open circuit voltage OCV and the closed circuit voltage CCV according to discharging of a lithium-ion secondary battery using spinel-type $Li_{1+x}Co_2O_4$ as its positive-electrode active material, disclosed in LITHIUM COBALT SPINEL OXIDE: A STRUCTURAL AND ELECTROCHEMICAL STUDY (ERIKA MEZA et al, J. Chil. Chem. Soc, 53, No 2 (2008), pages: 1494-1497). The vertical axis represents the voltage values of the open circuit voltage OCV and the closed circuit voltage CCV, and as it goes upward, the voltage values increase. The horizontal axis represents the amount of lithium in the positive-electrode active material, and as it goes more to the right, the amount increases. In other words, as it goes more to the right, the remaining power storage capacity decreases, and the integrated value of discharged power increases.

Figure 10:
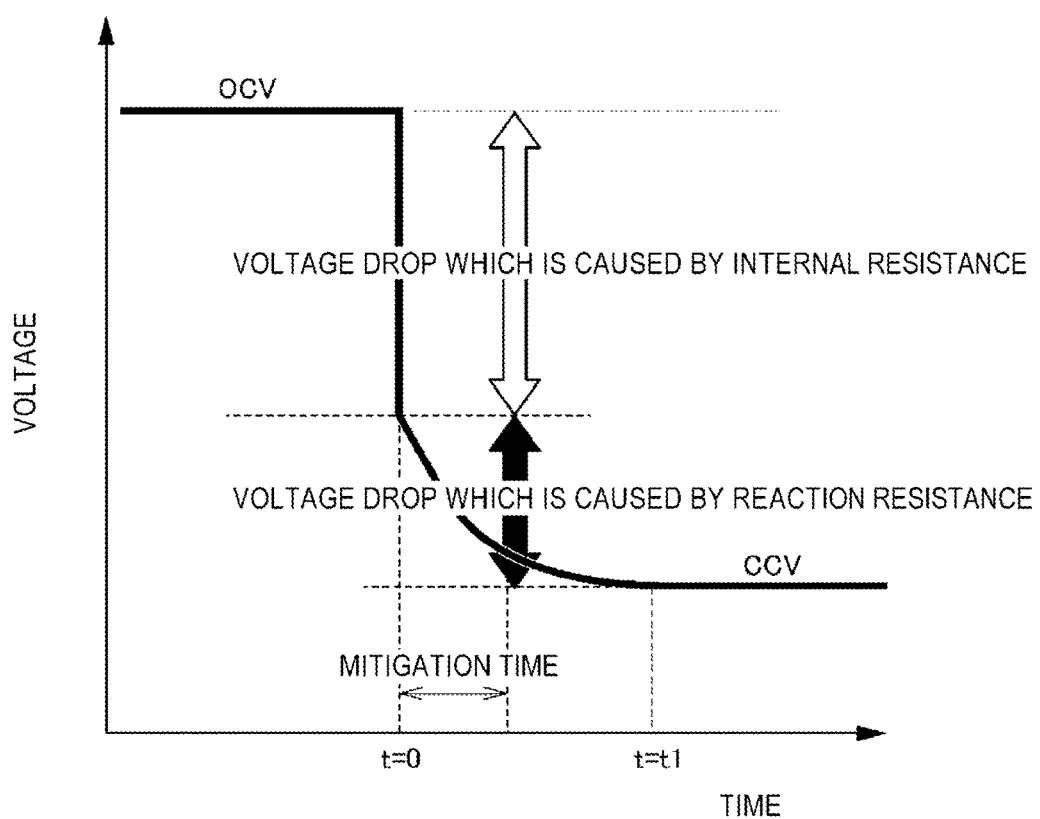
FIG. 10 is an explanatory view for explaining the relation between the difference between open circuit voltage and closed circuit voltage and internal resistance.

This relation is expressed as the graph of FIG. 10 having a vertical axis representing voltage and a horizontal axis representing time. The temporal change of the closed circuit voltage CCV in the equivalent circuit shown in FIG. 8 can be expressed as the following Expression 1 and Expression 2.

$$CCV(t) = E_{Batt} - I(t) * R_{imp.} - I(t) * R_{EDL} * \left\{1 - \exp\left(-\frac{t}{R_{EDL} * C_{EDL}}\right)\right\} \quad (1)$$

$$I(t) = \frac{E_{Batt}}{R_{imp.} + R_{EDL} * \left\{1 - \exp\left(-\frac{t}{R_{EDL} * C_{EDL}}\right)\right\} + R_{load}} \quad (2)$$

In Expression 2, $R_{load}$ represents the electric resistance value of the load 21.

Immediately after the switch 19 is turned on, the reaction resistance $R_{EDL}$ which is the primary delay component is negligible. In other words, immediately after the switch 19 is turned on, i.e. when t is 0, the difference between the open circuit voltage OCV and the closed circuit voltage CCV depends on the voltage drop which is caused by the inter-electrode internal resistance $R_{imp}$.

This can be expressed as Expression 3 from Expression 1 and Expression 2.

$$\frac{OCV - CCV(0)}{I(0)} = R_{imp.} \quad (3)$$

Meanwhile, in the case where t is sufficiently larger than the product of primary delay component mitigation times (time constants) $R_{EDL}$ and $C_{EDL}$ in Expression 1 and Expression 2, the difference between the open circuit voltage OCV and the closed circuit voltage CCV is attributable to the sum of the voltage drop caused by the inter-electrode internal resistance $R_{imp}$ and the voltage drop caused by the reaction resistance $R_{EDL}$.

This can be expressed as Expression 4 from Expression 1 and Expression 2.

$$\frac{OCV - CCV(t)}{I(t)} = R_{imp.} + R_{EDL} \quad (4)$$

By the way, in general, $R_{EDL}$ and $C_{EDL}$ are sufficiently small values. Therefore, it should be noted that the relation of Expression 4 is (approximately) established at a relatively early timing after the switch 19 is closed.

The power supply state diagnosis unit 52 acquires the internal resistance R on the basis of the open circuit voltage OCV of the power supply 12 and the closed circuit voltage CCV of the power supply 12. The closed circuit voltage CCV is, for example, an actual measurement value which is obtained by the voltage sensor 16.

The closed circuit voltage CCV may be an actual measurement value which is obtained when a sufficient time passes (t=t1) after the circuit is closed, or may be an actual measurement value which is obtained before the sufficient time passes (t<t1) after the circuit is closed. In the case where the actual measurement value which is obtained before the sufficient time passes (t<t1) after the circuit is closed is used as the closed circuit voltage CCV, it is possible to acquire the closed circuit voltage CCV earlier. In this case, the power supply state diagnosis unit 52 uses a threshold which is set on the basis of only the voltage drop caused by the inter-electrode internal resistance $R_{imp}$ which is the DC component, without considering the reaction resistance $R_{EDL}$ which is the primary delay component of the closed circuit voltage CCV, as a threshold which is compared with the acquired internal resistance R. In the present embodiment, as an example, the closed circuit voltage CCV which is obtained immediately after the circuit is closed may be used.

Meanwhile, in the case where the actual measurement value which is obtained when the sufficient time passes (t=t1) after the circuit is closed is used as the closed circuit voltage CCV, it is possible to accurately acquire the closed circuit voltage CCV. In this case, the power supply state diagnosis unit 52 uses a threshold which is set on the basis of the sum of the voltage drop caused by the inter-electrode internal resistance $R_{imp}$ and the voltage drop caused by the reaction resistance $R_{EDL}$ in consideration of the reaction resistance $R_{EDL}$ which is the primary delay component of the closed circuit voltage CCV, as the threshold which is compared with the acquired internal resistance R. However, the closed circuit voltage CCV is not limited to an actual measurement value, and an estimate value may be used. By estimating the closed circuit voltage CCV, it is possible to make it unnecessary to actually measure the closed circuit voltage CCV. Since the closed circuit voltage CCV serves as a primary delay system, it takes a very long time to settle down in a complete stationary state. For the purpose of convenience, in the present embodiment, the closed circuit voltage CCV which is obtained when the mitigation time passes or a time which is the sum of the mitigation time and a predetermined value passes after the circuit is closed may be used.

Also, the power supply state diagnosis unit 52 may acquire the closed circuit voltage CCV using current smaller than the current when power is discharged to the load 21 in order to generate an aerosol, or may use a constant as the current value in order to derive the internal resistance R. In the case of using an actual measurement value as the current value, it is possible to measure the current value using a current sensor (not shown in the drawings). If the closed circuit voltage CCV is acquired using small current, it is possible to reduce the deviation between the actual current value and I which is treated as a constant in Expression 3 and Expression 4. Also, it is possible to restrain an aerosol from being generated during acquisition of the closed circuit voltage CCV.

If small current smaller than the current when power is discharged to the load 21 in order to generate an aerosol is applied in order to acquire the closed circuit voltage CCV, it is possible to reduce the power consumption for acquiring the closed circuit voltage CCV. Also, if a constant is used as the current value in order to derive the internal resistance R, it is not required to actually measure the current value. For example, a constant can be used as the current value by acquiring the closed circuit voltage CCV in the course of constant current control. As a result, the current sensor becomes unnecessary. Therefore, it is possible to reduce the size, weight, and cost of the aerosol inhaler 1.

Now, the control flow of the deterioration diagnosis control will be described with reference to FIG. 11 and FIG. 12.

First of all, the aerosol generation request detecting unit 51 detects a request for aerosol generation on the basis of the output result of the inhalation sensor 15 (STEP S1). By acquiring the deteriorated state of the power supply 12 in response to a user's request for aerosol generation, it is possible to make the user recognize the deterioration determination result.

In the case where the aerosol generation request detecting unit 51 has detected the request for aerosol generation, the open circuit voltage OCV is acquired (STEP S2); whereas in the case where the aerosol generation request detecting unit 51 has not detected the request for aerosol generation, the process of STEP S1 is repeated. After the open circuit voltage OCV is acquired in STEP S2, the switch 19 is turned on (STEP S3), and the closed circuit voltage CCV is acquired (STEP S4), and the current value is acquired (STEP S5). However, STEP S4 may be performed after STEP S5.

After the current value is acquired, the internal resistance R ($R_{imp}$, or the sum of $R_{imp}$ and $R_{EDL}$) is derived from Expression 1 or Expression 2, and the derived internal resistance R is compared with a threshold Th1 (STEP S6). In the case where the internal resistance R is smaller than the threshold Th1 ("Yes" in STEP S6), the power supply state diagnosis unit 52 determines that the power supply 12 is in the normal state (STEP S7), and the power control unit 53 performs PWM control to generate an aerosol (STEP S8). Meanwhile, in the case where the internal resistance R is equal to or larger than the threshold Th1 ("No" in STEP S6), the power supply state diagnosis unit determines that the power supply 12 has deteriorated (STEP S9), and the notification control unit 54 notifies the user that it is required to replace the power supply 12.

If the closed circuit voltage CCV acquired in STEP S4 is the closed circuit voltage acquired immediately after the switch 19 was turned on, i.e. when t was 0, the internal resistance R is the inter-electrode internal resistance $R_{imp}$. For this reason, the threshold Th1 is a threshold which is set on the basis of the voltage drop caused by the inter-electrode internal resistance $R_{imp}$. Meanwhile, if the acquired closed circuit voltage CCV is the closed circuit voltage CCV acquired when the mitigation time passed, i.e. when t was t1, the internal resistance R is the sum of the inter-electrode internal resistance $R_{imp}$ and the reaction resistance $R_{EDL}$. For this reason, the threshold Th1 is a threshold which is set on the basis of the sum of the voltage drop caused by the inter-electrode internal resistance $R_{imp}$ and the voltage drop caused by the reaction resistance $R_{EDL}$.

This deterioration diagnosis control on the power supply 12 is performed in response to the user's request for aerosol generation before generation of an aerosol. Therefore, it is possible to avoid use of the deteriorated power supply 12. Also, turning on of the switch 19 for acquiring the closed circuit voltage CCV in STEP S3 is used for other purposes (here, for PWM control for applying the closed circuit voltage CCV to the load 21). Therefore, it is possible to prevent current from flowing in the circuit only for deterioration diagnosis on the power supply 12.

Hereinafter, modifications of the above-described deterioration diagnosis control will be described; however, descriptions of the same steps as those of FIG. 11 will not be made.

(Deterioration Diagnosis Control of First Modification)

Figure 13:
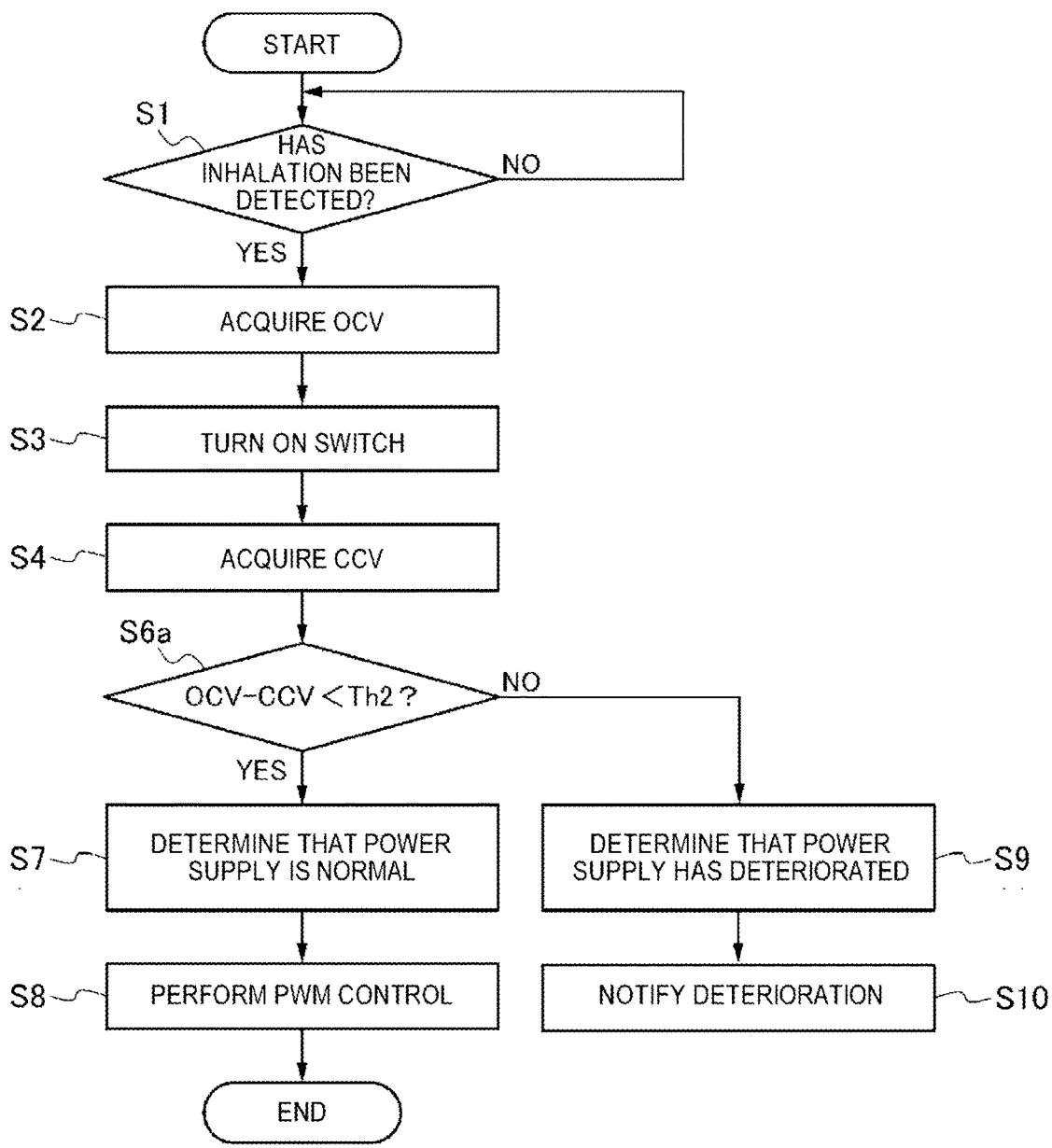
FIG. 13 is a control flow chart of deterioration diagnosis control of a first modification.

Also, the power supply state diagnosis unit 52 can use a constant as the current value in order to derive the internal resistance R as described above. In the case of using a constant as the current value, as shown in FIG. 13, after the closed circuit voltage CCV is acquired in STEP S4, it is possible to proceed to the next process (STEP S6a) without performing STEP S5 of acquiring the current value. Also, in the case where acquisition of the current value is not performed, the internal resistance R may be derived, or the internal resistance R may not be derived.

Figure 11:
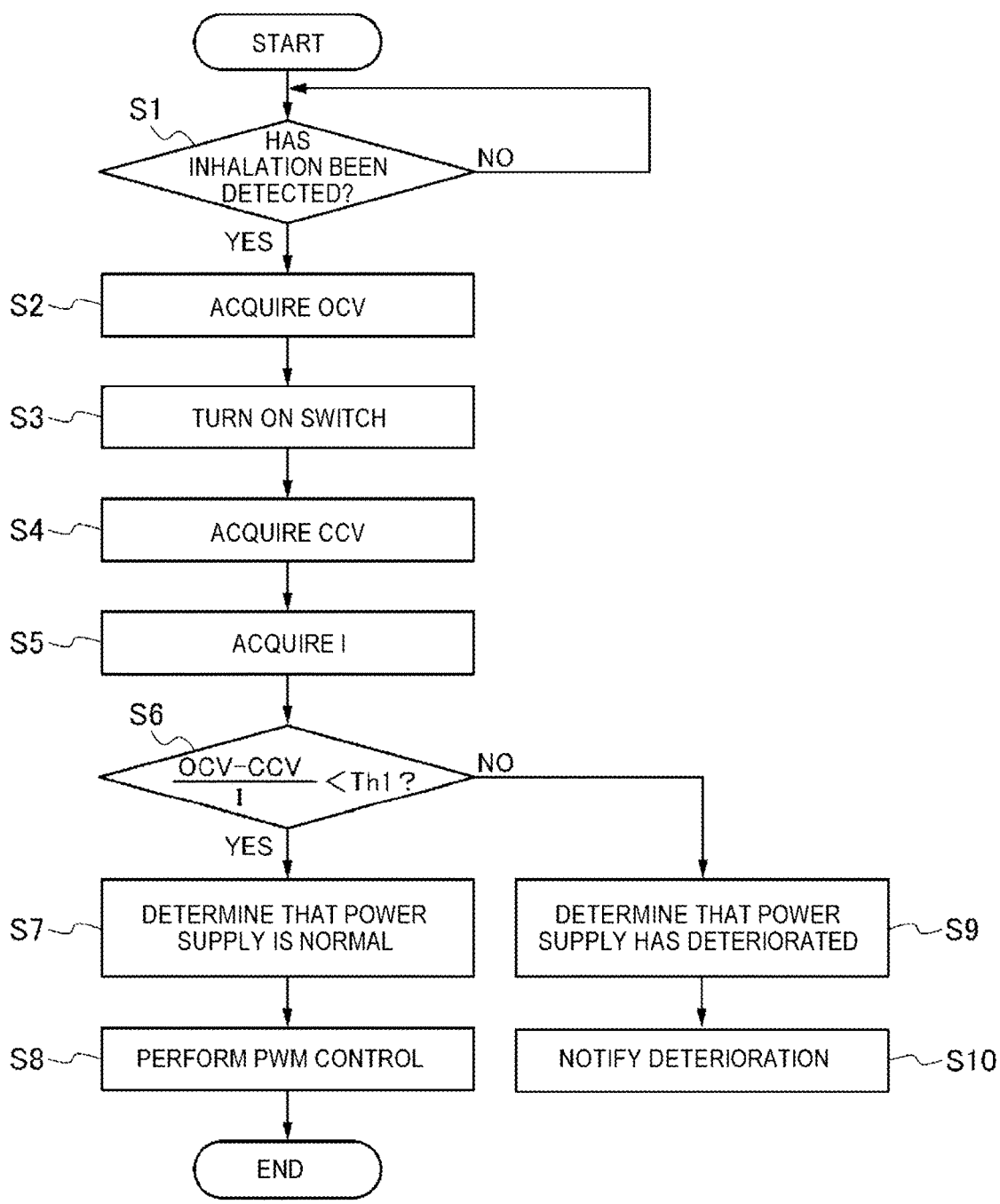
FIG. 11 is a control flow chart of deterioration diagnosis control.
Figure 12:
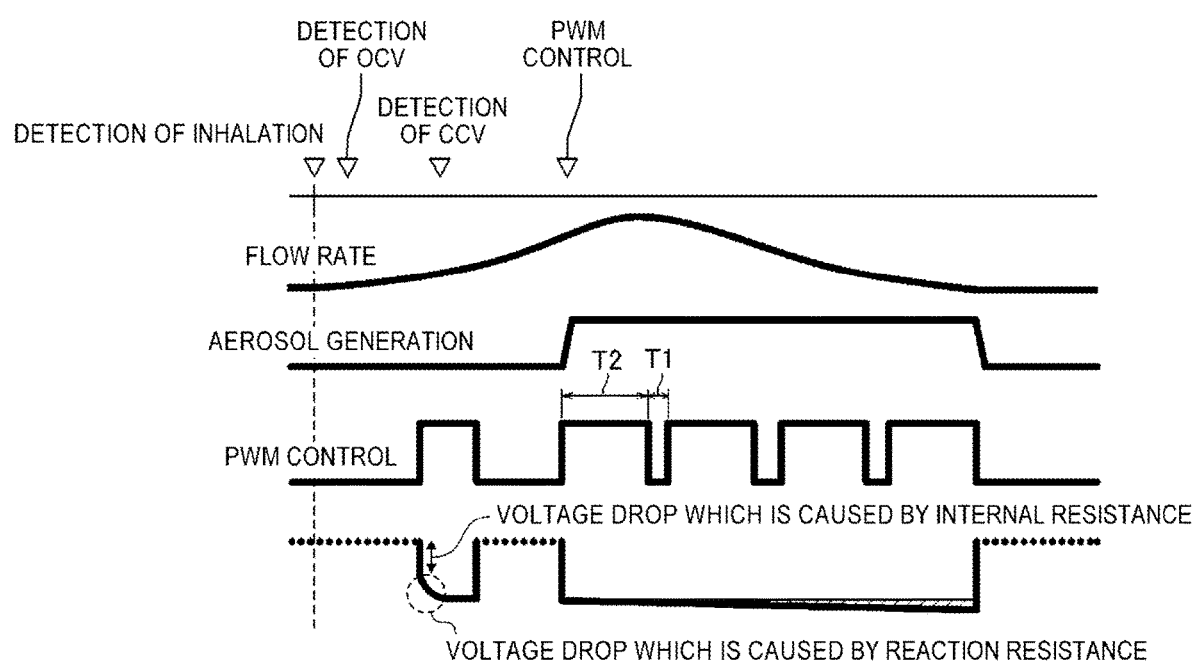
FIG. 12 is a timing chart of the deterioration diagnosis control of FIG. 11.

In the case of deriving the internal resistance R, the internal resistance R is derived on the basis of the value obtained by dividing the difference between the open circuit voltage OCV and the closed circuit voltage CCV by the constant, and similarly in STEP S6 of FIG. 11, the derived internal resistance R is compared with the threshold Th1.

Meanwhile, in the case where the internal resistance R is not derived, the difference between the open circuit voltage OCV and the closed circuit voltage CCV, and a threshold Th2 obtained by adding the current value to the threshold Th1 may be compared. Like this, even if the internal resistance R is not derived, the deteriorated state of the power supply 12 may be acquired on the basis of an electric parameter (the closed circuit voltage CCV) of the power supply 12 when it is discharged and an electric parameter (the open circuit voltage OCV) of the power supply 12 when it is not discharged. Even in this case, it is possible to appropriately grasp the deteriorated state of the power supply 12. Also, in order to acquire the closed circuit voltage CCV, the current value when the power supply 12 is discharged may be measured in advance, and be used as the constant.

The threshold Th2 may be a value obtained by multiplying a value which the internal resistance R can take only in the case where the power supply 12 is in the deteriorated state by the constant considered as the current value. If the threshold Th2 which is set as described above is recorded in the memory 18 in advance, the division process in STEP S6 becomes unnecessary. Therefore, it is possible to increase the speed of the process of STEP S6a.

(Deterioration Diagnosis Control of Second Modification)

Figure 14:
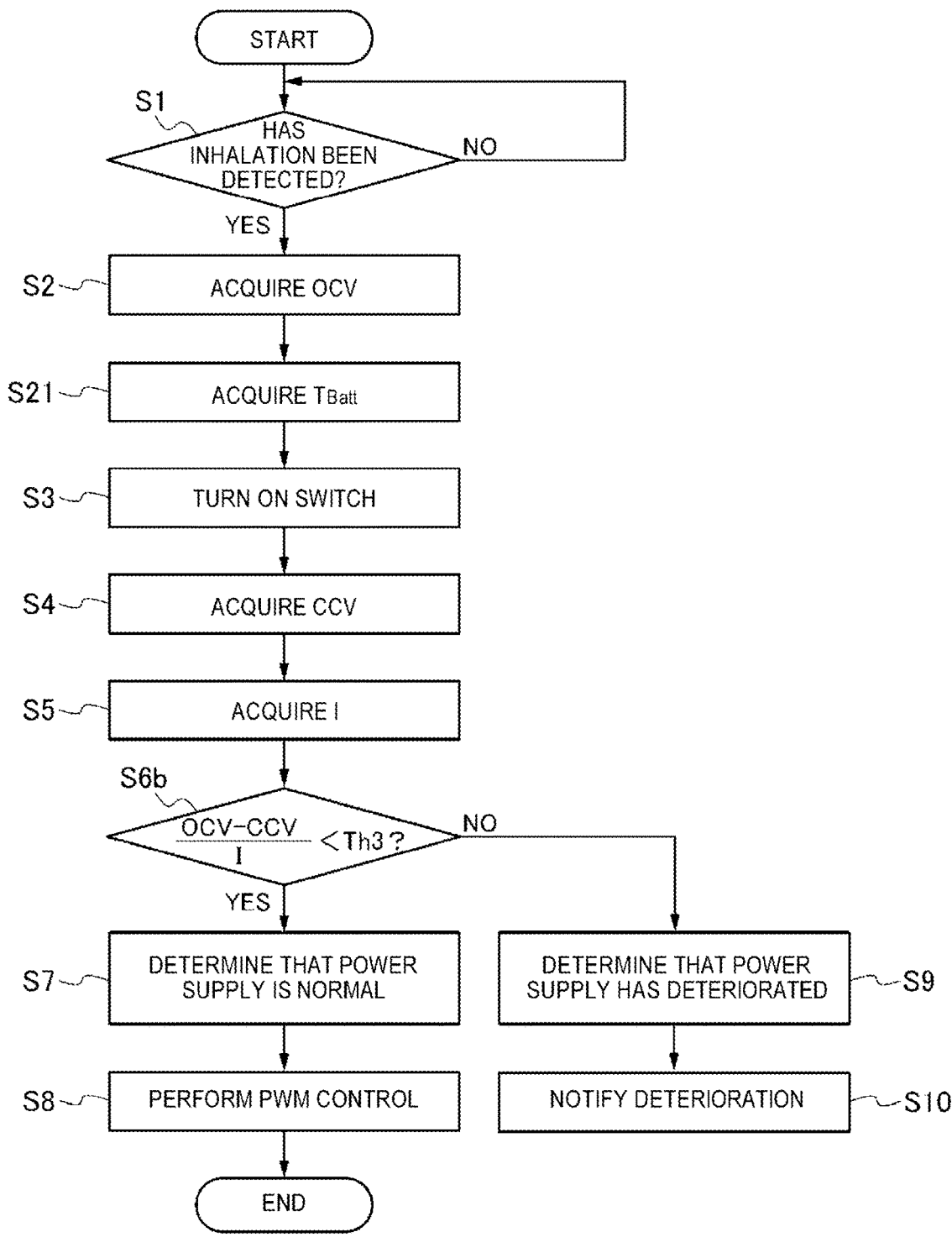
FIG. 14 is a control flow chart of deterioration diagnosis control of a second modification.

Also, since the internal resistance R depends on temperature, the power supply state diagnosis unit 52 may acquire the temperature of the power supply 12 from the temperature sensor 17, and set a threshold on the basis of the information on the temperature of the power supply 12. In the embodiment shown in FIG. 14, after the open circuit voltage OCV is acquired in STEP S2, the temperature $T_{Batt}$ is acquired (STEP S21) before the switch 19 is turned on in STEP S3. However, acquisition of the temperature of the power supply 12 is not limited thereto, and can be performed at any time. After the temperature of the power supply 12 is acquired, in STEP S6b, the derived internal resistance R and a threshold Th3 set on the basis of the temperature of the power supply 12 are compared. In other words, since the internal resistance R increases as the temperature of the power supply 12 lowers, the threshold Th3 is set to be larger as the temperature of the power supply 12 lowers. If the temperature dependence of the internal resistance R is considered as described above, it is possible to more appropriately acquire deterioration of the power supply 12.

In the present embodiment, the threshold Th3 is corrected using the temperature $T_{Batt}$. Alternatively, the internal resistance R which is derived in STEP S6b may be corrected. As an example, when the temperature of the power supply 12 is low, correction may be performed by setting a large current value I or multiplying the internal resistance R by a predetermined coefficient smaller than 1. It is preferable that the correction amount of the internal resistance R increase as the temperature of the power supply 12 lowers. In other words, it is preferable to increase the current value I or decrease the coefficient, by which the internal resistance is multiplied, as the temperature of the power supply 12 lowers.

Also, it is preferable that the temperature sensor 17 be disposed close to the power supply 12; however, the temperature sensor may be disposed far from the power supply 12. In this case, the temperature $T_{Batt}$ of the power supply 12 may be obtained by correcting the measurement value of the temperature sensor 17 in consideration of the distance between the power supply 12 and the temperature sensor 17.

(Deterioration Diagnosis Control of Third Modification)

Also, the power supply state diagnosis unit 52 may use at least one of the acquired open circuit voltage OCV and the acquired closed circuit voltage CCV for other purposes. Here, the case of using the acquired open circuit voltage OCV and the acquired closed circuit voltage CCV to determine the amount of power (SOC) stored in the power supply 12 is taken as an example. In the embodiment shown in FIG. 15, after the open circuit voltage OCV is acquired in STEP S2, the acquired open circuit voltage OCV is compared with a threshold Th4 (see FIG. 9) which is a value at which charging is required (STEP S20). In the case where the open circuit voltage OCV is equal to or smaller than the threshold Th4 ("No" in STEP S20), the notification control unit 54 notifies the user that it is required to charge the power supply 12 (STEP S11).

Also, after the closed circuit voltage CCV is acquired in STEP S4, the acquired closed circuit voltage CCV is compared with a threshold Th5 (see FIG. 9) which is a value at which charging is required (STEP S40). In the case where the closed circuit voltage CCV is equal to or smaller than the threshold Th5 ("No" in STEP S40), the notification control unit 54 notifies the user that it is required to charge the power supply 12 (STEP S11). In this way, it is possible to perform determination on the amount of stored power together with determination on deterioration of the power supply 12. Also, in the embodiment shown in FIG. 15, the case of using the acquired open circuit voltage OCV and the acquired closed circuit voltage CCV to determine the amount of power stored in the power supply 12 is shown as an example. However, only any one of them may be used to determine the amount of power stored in the power supply 12, or they may be used for other purposes.

As an example of other purposes, the acquired open circuit voltage OCV and the acquired closed circuit voltage CCV may be used to set a duty ratio for the above-described PWM control or an OFF time in PFM control.

(Failure Diagnosis Control)

Also, the power supply state diagnosis unit 52 may diagnose not only deterioration but also failure on the power supply 12. As described above, the internal resistance value increases as deterioration of the power supply 12 progresses. By the way, if the power supply 12 fails, the internal resistance of the power supply 12 may show an extremely large or small value. As an example, if the power supply 12 is short-circuited, since excessively large current may flow, the internal resistance shows an extremely small value. Also, as another example, if the electrolytic solution of the power supply 12 decreases or runs out, since current rarely flows, the internal resistance of the power supply 12 shows an extremely large value.

Using this phenomenon, the power supply state diagnosis unit 52 may detect failure of the power supply 12 attributable to short-circuiting or the like by detecting an internal resistance value smaller than the internal resistance values which the power supply 12 can take when it is brand new. Also, the power supply state diagnosis unit 52 may detect failure of the power supply 12 attributable to decrease or depletion of the electrolytic solution or the like by detecting an internal resistance value sufficiently larger than the threshold for deterioration detection.

The notification control unit 54 may control the notifying unit 45 on the basis of detection of failure of the power supply 12 by the power supply state diagnosis unit 52 such that the notifying unit notifies the timing to replace the power supply 12.

However, the present invention is not limited to the above-described embodiment, and modifications, improvements, etc. can be made properly.

In this specification, at least the following inventions (1) to (22) are disclosed.

(1) A power supply unit for an aerosol inhaler, the power supply unit comprising:

a power supply that is able to discharge power to a load for generating an aerosol from an aerosol source; and a control unit that is configured to control the power supply, wherein the control unit acquires a deteriorated state or a failure state of the power supply based on an internal resistance of the power supply.

According to (1), the internal resistance of the power supply is acquired using that the internal resistance of the power supply increases as deterioration of the power supply progresses. Therefore, it is possible to appropriately grasp the deteriorated state or the failure state of the power supply in a shorter time.

(2) The power supply unit according to (1), wherein the control unit acquires the internal resistance based on an open circuit voltage of the power supply and a closed circuit voltage of the power supply.

According to (2), since the open circuit voltage of the power supply and the closed circuit voltage of the power supply are acquired, it is possible to easily derive the internal resistance of the power supply.

(3) The power supply unit according to (2), wherein the closed circuit voltage is an actual measurement value.

According to (3), since the closed circuit voltage of the power supply acquired by a voltmeter is used, it is possible to improve the accuracy of derivation of the internal resistance as compared to the case of using an estimate value.

(4) The power supply unit according to (3), wherein the closed circuit voltage is an actual measurement value which is obtained when a predetermined time passes after a circuit is closed.

According to (4), since the closed circuit voltage is measured after the closed circuit voltage is stabilized, it is possible to accurately acquire the closed circuit voltage.

(5) The power supply unit according to (3), wherein the control unit acquires the deteriorated state or the failure state of the power supply based on comparison between the internal resistance and a threshold which is set without considering a primary delay component of the closed circuit voltage.

According to (5), since the threshold for performing deterioration determination or failure determination is set without considering the primary delay component of the closed circuit voltage even before the closed circuit voltage is stabilized, it is possible to acquire the deteriorated state or the failure state of the power supply, earlier and more accurately.

(6) The power supply unit according to (3), wherein the control unit acquires the deteriorated state or the failure state of the power supply based on comparison between the internal resistance and a threshold which is set based on only a DC component of the internal resistance.

According to (6), since deterioration determination or failure determination is performed based on comparison between the internal resistance and the threshold which is set based on only the DC component of the internal resistance, it is possible to acquire the deteriorated state or the failure state of the power supply, earlier and more accurately.

(7) The power supply unit according to any one of (3) to (6), wherein the control unit acquires the closed circuit voltage using a current smaller than a current when power is discharged to the load in order to generate an aerosol.

According to (7), since the small current is used, it is possible to reduce power consumption for acquiring the closed circuit voltage. Also, it is possible to restrain an aerosol from being generated when the closed circuit voltage is acquired.

(8) The power supply unit according to (2), wherein the closed circuit voltage is an estimate value.

According to (8), since the closed circuit voltage is estimated, it is not required to actually measure the closed circuit voltage. Therefore, while it is possible to reduce power consumption, it is possible to restrain an aerosol from being generated when the closed circuit voltage is acquired.

(9) The power supply unit according to any one of (2) to (8), wherein the control unit derives the internal resistance based on a value obtained by dividing a difference between the open circuit voltage and the closed circuit voltage by a constant, or the control unit acquires the deteriorated state or the failure state of the power supply based on comparison between a difference between the open circuit voltage and the closed circuit voltage and a value obtained by multiplying a value which the internal resistance can take only in a case where the power supply is in the deteriorated state or the failure state by a constant.

According to (9), since the constant is used as the current value to derive the internal resistance, it is not required to actually measure the current value. Therefore, a current sensor is not required. Therefore, it is possible to reduce the weight, cost, and size of the aerosol inhaler. Further, it is possible to more quickly perform derivation of the internal resistance, and so on.

(10) The power supply unit for an aerosol inhaler according to (9), wherein:

the constant is set based on a current value which the power supply discharges when the closed circuit voltage is acquired.

According to (10), since the constant is set based on the current value which the power supply discharges when the closed circuit voltage is acquired, it is possible to more accurately perform derivation of the internal resistance, and so on.

(11) The power supply unit according to any one of (1) to (10), wherein the control unit acquires the deteriorated state or the failure state in response to a request for aerosol generation.

According to (11), since the deteriorated state of the power supply is acquired in response to the user's request for aerosol generation, it is possible to make the user recognize the result of deterioration determination. Also, it is possible to perform deterioration determination at an appropriate timing while suppressing power consumption which may be caused by excessive deterioration determination.

(12) The power supply unit according to any one of (1) to (11), wherein the control unit acquires the deteriorated state or the failure state before aerosol generation.

According to (12), since the deteriorated state or the failure state is acquired before aerosol generation, it is possible to prevent use of the power supply which is in the deteriorated state.

(13) The power supply unit according to any one of (1) to (12), wherein the control unit acquires the deteriorated state or the failure state of the power supply, based on comparison between the internal resistance and a threshold which is set based on a temperature of the power supply, or comparison between a threshold and the internal resistance of the power supply which is corrected based on a temperature of the power supply.

According to (13), since the temperature dependence of the internal resistance is considered, it is possible to more appropriately acquire the deteriorated state or the failure state of the power supply.

(14) The power supply unit according to (13), wherein an amount of correction by which the internal resistance is corrected based on the temperature of the power supply or the threshold which is set based on the temperature of the power supply increases as the temperature of the power supply lowers.

According to (14), since the threshold or the amount of correction for deterioration determination or failure determination is increased as the temperature of the power supply lowers, it is possible to more appropriately acquire the deteriorated state or the failure state of the power supply in consideration of the increase in the internal resistance when the temperature is low.

(15) The power supply unit according to any one of (2) to (9), wherein the control unit uses at least one of the open circuit voltage and the closed circuit voltage for another purpose.

According to (15), since the acquired open circuit voltage and/or the acquired closed circuit voltage is used for another purpose, it is possible to prevent current from flowing only for deterioration determination or failure determination on the power supply.

(16) The power supply unit according to (15), wherein the another purpose is determination on an amount of power stored in the power supply.

According to (16), since the acquired open circuit voltage and/or the acquired closed circuit voltage is used for determination on the amount of power stored in the power supply, it is possible to perform determination on the amount of stored together with determination on deterioration of the power supply.

(17) The power supply unit according to (15), wherein the another purpose is PWM control or PFM control for discharging power to the load in order to generate an aerosol.

According to (17), since the closed circuit voltage is used in PWM control or PFM control for discharging power to the load, it is possible to prevent current from flowing in the circuit only for deterioration determination or failure determination on the power supply.

(18) A control method of a power supply unit for an aerosol inhaler, the power supply unit including a power supply that is able to discharge power to a load for generating an aerosol from an aerosol source, the control method comprising:

acquiring a deteriorated state or a failure state of the power supply based on an internal resistance of the power supply.

According to (18), since the internal resistance of the power supply is derived using that the internal resistance of the power supply increases as deterioration of the power supply progresses, it is possible to appropriately grasp the deteriorated state or the failure state of the power supply in a shorter time.

(19) A control program of a power supply unit for an aerosol inhaler, the power supply unit including a power supply that is able to discharge power to a load for generating an aerosol from an aerosol source, the control program making a computer execute:

a control step of acquiring a deteriorated state or a failure state of the power supply based on an internal resistance of the power supply.

According to (19), since the internal resistance of the power supply is derived using that the internal resistance of the power supply increases as deterioration of the power supply progresses or due to failure of the power supply, it is possible to appropriately grasp the deteriorated state or the failure state of the power supply in a shorter time.

(20) A power supply unit for an aerosol inhaler, the power supply unit comprising:

a power supply that is able to discharge power to a load for generating an aerosol from an aerosol source; and a control unit that is configured to control the power supply, wherein the control unit acquires a deteriorated state or a failure state of the power supply based on a difference between an electric parameter of the power supply when the power supply is discharged and an electric parameter of the power supply when the power supply is not discharged.

According to (20), since the deteriorated state or the failure state of the power supply is acquired based on the difference between the electric parameter of the power supply when the power supply is discharged and the electric parameter of the power supply when the power supply is not discharged, it is possible to appropriately grasp the deteriorated state or the failure state of the power supply.

(21) A control method of a power supply unit for an aerosol inhaler, the power supply unit including a power supply that is able to discharge power to a load for generating an aerosol from an aerosol source, the control method comprising:

acquiring a deteriorated state or a failure state of the power supply based on a difference between an electric parameter of the power supply when the power supply is discharged and an electric parameter of the power supply when the power supply is not discharged.

According to (21), since the deteriorated state or the failure state of the power supply is acquired based on the difference between the electric parameter of the power supply when the power supply is discharged and the electric parameter of the power supply when the power supply is not discharged, it is possible to appropriately grasp the deteriorated state or the failure state of the power supply.

(22) A control program of a power supply unit for an aerosol inhaler, the power supply unit including a power supply that is able to discharge power to a load for generating an aerosol from an aerosol source, the control program making a computer execute:

a control step of acquiring a deteriorated state or a failure state of the power supply based on a difference between an electric parameter of the power supply when the power supply is discharged and an electric parameter of the power supply when the power supply is not discharged.

According to (22), since the deteriorated state or the failure state of the power supply is acquired based on the difference between the electric parameter of the power supply when the power supply is discharged and the electric parameter of the power supply when the power supply is not discharged, it is possible to appropriately grasp the deteriorated state or failure state of the power supply.

According to (1), and (18) to (23), since the deteriorated state or the failure state of the power supply is acquired based on the internal resistance of the power supply, or the deteriorated state or the failure state of the power supply is acquired based on the difference between the electric parameter of the power supply when the power supply is discharged and the electric parameter of the power supply when the power supply is not discharged, it is possible to appropriately grasp the deteriorated state or the failure state of the power supply. Therefore, it is possible to prompt the user or the like to replace the power supply at an appropriate timing. Therefore, there is energy saving effect in which it is possible to maximize the period for which it is possible to use the power supply without replacing with a brand new one.

According to the present invention, on the basis that the internal resistance of a power supply increases as the power supply deteriorates, the internal resistance or the like of a power supply is derived, whereby it is possible to appropriately grasp the deteriorated state or failure state of the power supply in a shorter time.

What is claimed is:

1. A power supply unit for an aerosol inhaler, the power supply unit comprising:

a power supply configured to discharge power to a load for generating an aerosol from an aerosol source;
a switch that is disposed on a power transmission path between the power supply and the load; and
a controller that is configured to control the power supply and the switch,
wherein:
the controller acquires an open circuit voltage of the power supply,
after acquiring the open circuit voltage, the controller measures a closed circuit voltage of the power supply in a discharging state using a current smaller than a current when power is discharged to the load in order to generate the aerosol,
the controller acquires the closed circuit voltage of the power supply immediately after the switch is turned off with the current smaller than the current when power is discharged to the load in order to generate the aerosol,
the controller acquires an internal resistance of the power supply based on the closed circuit voltage and the open circuit voltage of the power supply, and
the controller acquires a deteriorated state or a failure state of the power supply based on the internal resistance.

2. The power supply unit according to claim 1, wherein the controller acquires the deteriorated state or the failure state of the power supply based on a comparison between a threshold which is set without considering a primary delay component of the closed circuit voltage, and the internal resistance.

3. The power supply unit according to claim 1, wherein the controller acquires the deteriorated state or the failure state of the power supply based on a comparison between a threshold which is set based on only a DC component of the internal resistance, and the internal resistance.

4. The power supply unit according to claim 1, wherein the controller derives the internal resistance based on a value obtained by dividing a difference between the open circuit voltage and the closed circuit voltage by a constant.

5. The power supply unit according to claim 4, wherein the constant is set based on a current value which the power supply discharges when the closed circuit voltage is acquired.

6. The power supply unit according to claim 1, wherein the controller acquires the deteriorated state or the failure state before aerosol generation.

7. The power supply unit according to claim 1, wherein the controller comprises an electronic circuit.

8. The power supply unit according to claim 1, wherein the controller comprises a processor or computer.

9. A power supply unit for an aerosol inhaler, the power supply unit comprising:

a power supply that configured to discharge power to a load for generating an aerosol from an aerosol source;
a switch that is disposed on a power transmission path between the power supply and the load; and
a controller that is configured to control the power supply and the switch,
wherein:
the controller acquires an open circuit voltage prior to acquiring a closed circuit voltage of the power supply, and acquires an internal resistance based on the open circuit voltage of the power supply, and based on the closed circuit voltage of the power supply in a discharging state,
the controller acquires the closed circuit voltage of the power supply immediately after the switch is turned off with the current smaller than the current when power is discharged to the load in order to generate the aerosol,
the controller acquires a deteriorated state or a failure state of the power supply based on the internal resistance, and
the controller determines an amount of power stored in the power supply based on at least one of the open circuit voltage and the closed circuit voltage.

10. The power supply unit according to claim 9, wherein the controller discharges power to the load by pulse width modulation (PWM) control or pulse frequency modulation (PFM) control in order to generate the aerosol.

11. A control method of a power supply unit for an aerosol inhaler, the power supply unit including a power supply that is able to discharge power to a load for generating an aerosol from an aerosol source, the control method comprising:

acquiring an open circuit voltage of the power supply;

after acquiring the open circuit voltage, measuring a closed circuit voltage of the power supply in a discharging state using a current smaller than a current when power is discharged to the load in order to generate the aerosol;

acquiring an internal resistance of the power supply based on the closed circuit voltage and an open circuit voltage of the power supply; and acquiring a deteriorated state or a failure state of the power supply based on the internal resistance, wherein the measuring the closed circuit voltage includes acquiring the closed circuit voltage of the power supply immediately after a switch is turned off with the current smaller than the current when power is discharged to the load in order to generate the aerosol, the switch being disposed on a power transmission path between the power supply and the load.

\* \* \* \* \*